United States Patent
Vogel

(10) Patent No.: US 8,894,495 B1
(45) Date of Patent: Nov. 25, 2014

(54) MULTI-PART SYSTEM FOR DEPLOYING NEAR FIELD COMMUNICATIONS IN ORDER TO FACILITATE THE ABILITY OF A VISUALLY-IMPAIRED PERSON TO ASCERTAIN THE IDENTITY OF A PLAYING CARD

(71) Applicant: David Saul Vogel, Palm Beach Gardens, FL (US)

(72) Inventor: David Saul Vogel, Palm Beach Gardens, FL (US)

( * ) Notice: Subject to any disclaimer, the term of this patent is extended or adjusted under 35 U.S.C. 154(b) by 0 days.

(21) Appl. No.: 14/168,013

(22) Filed: Jan. 30, 2014

Related U.S. Application Data

(60) Provisional application No. 61/925,000, filed on Jan. 8, 2014.

(51) Int. Cl.
  *G06K 9/00* (2006.01)
  *G06F 17/00* (2006.01)
  *H04B 5/00* (2006.01)
  *A61F 9/08* (2006.01)
  *G09B 21/00* (2006.01)

(52) U.S. Cl.
  CPC ............ *H04B 5/0025* (2013.01); *H04B 5/0056* (2013.01); *A61F 9/08* (2013.01); *G09B 21/006* (2013.01)
  USPC ............................................. 463/47; 434/116

(58) Field of Classification Search
  CPC ................................. G09B 21/006; A61F 9/08
  USPC ................... 434/112, 116; 463/13, 37, 40, 47
  See application file for complete search history.

(56) References Cited

U.S. PATENT DOCUMENTS

| | | | |
|---|---|---|---|
| 5,429,507 A * | 7/1995 | Kaplan | ............................ 463/30 |
| 6,159,013 A * | 12/2000 | Parienti | ......................... 434/114 |
| 7,727,060 B2 | 6/2010 | Mills | |
| 2007/0052167 A1 | 3/2007 | Galatan | |
| 2013/0178264 A1 | 7/2013 | Vilpas | |

FOREIGN PATENT DOCUMENTS

| | | |
|---|---|---|
| DE | 102007007022 A1 | 8/2008 |
| EP | 1713027 A2 | 10/2006 |

OTHER PUBLICATIONS

Maria L. Toro, Playing Cards Reader for People with Visual Impairments, Rehabilitation Engineering and Assistive Technology Society of North America, May 13, 2010, (5 Pages).

* cited by examiner

*Primary Examiner* — David L Lewis
*Assistant Examiner* — Robert Mosser
(74) *Attorney, Agent, or Firm* — Lloyd McAulay

(57) ABSTRACT

A multi-part system utilizing an active-passive configuration of Near Field Communications ("NFC") in order to facilitate the ability of a visually-impaired person to: (i) ascertain the specific rank and suit of a playing card; and (ii) maintain privacy of information regarding the identity of the card. The present invention comprises: (i) a passive "NFC Tag" that is embedded within a playing card and that is encoded with the information necessary to identify the rank and suit of the card; and (ii) an active "NFC Reader" that is disposed within a wearable sheath and is designed to receive and to relay the said information to a wearable earpiece; and (iii) a said earpiece that deploys a combination of hardware and software in order to convert the said information to an audible signal that identifies the card for a user of the invention.

6 Claims, 4 Drawing Sheets

MULTI-PART SYSTEM FOR DEPLOYING NEAR FIELD COMMUNICATIONS IN ORDER TO FACILITATE THE ABILITY OF A VISUALLY-IMPAIRED PERSON TO ASCERTAIN THE IDENTITY OF A PLAYING CARD

CROSS REFERENCE TO RELATED APPLICATIONS

This utility patent application claims the benefit of U.S. Provisional Patent Application No. 61/925,000, filed Jan. 8, 2014.

STATEMENT REGARDING FEDERALLY SPONSORED RESEARCH OR DEVELOPMENT PERTAINING TO THE INVENTION

Not applicable.

REFERENCE TO SEQUENCE LISTING, A TABLE, OR A COMPUTER PROGRAM LISTING COMPACT DISC APPENDIX

Not applicable.

REFERENCES CITED

U.S. Patent Documents

| U.S. patent DOCUMENTS | | | |
|---|---|---|---|
| 7,727,060 | B2 | Jun. 2010 | Mills |
| 20070052167 | A1 | Mar. 2007 | Galatan |
| 20130178264 | A1 | Jul. 2013 | Vilpas |

Foreign Patent Documents

| FOREIGN patent DOCUMENTS | | | | |
|---|---|---|---|---|
| EP | 1713027 | A2 | Oct. 2006 | Koyama, et al. |
| DE | 102007007022 | A1 | Aug. 2008 | Ernst |

Other Publications

Playing Cards Reader for People with Visual Impairments, 13 May 2010, http://aac-rerc.psu.edu/wordpressmu/RESNA-SDC/2010/05/13/playing-cards-reader-for-people-with-visual-impairments-university-of-pittsburgh-2/

FIELD OF THE INVENTION

This invention relates to the field of the deployment of Near Field Communications ("NFC") in order to facilitate the ability of a visually-impaired person to ascertain the rank and the suit of an individual playing card.

BACKGROUND OF THE INVENTION

1. Field of the Endeavor to which the Present Invention Pertains

The activity of playing card games is nearly universal. Because the nature of playing card games requires a player to be able to ascertain the identity (i.e., the specific rank and the suit) of at least one individual playing card during the course of any given game, and also typically requires the said player to do so in a way that maintains privacy of information regarding the identity of the said card, it is necessary for the said player to have some way of accomplishing these goals. For a person whose eyesight is adequate for these purposes, accomplishing these objectives generally presents few practical problems. However, for a person whose eyesight is compromised to the point where achieving the aforementioned objectives is impossible without some type of external assistance, there are only three practical solutions currently available.

The first solution is the utilization of playing cards that are equipped with a plurality of tactile identifiers—Braille is the most popular of this type of playing card. Each individual card typically has a plurality of protrusions disposed upon the surface of the card. Said protrusions enable a visually-impaired player to ascertain the identity of a card by physically touching (typically, with at least one finger of a hand) the said protrusions. However, the use of Braille cards presents a number of practical difficulties:
  (i) excessive wear and tear with respect to the cards could impair the ability of a said visually-impaired person to read the cards properly; or
  (ii) Braille cards may be damaged easily by mechanical card-shufflers; or
  (iii) the presence of the physical protrusions that are disposed upon Braille cards could lead to the sacrifice of privacy of information regarding the identity of the cards because opponents of a said visually-impaired player who possess adequate eyesight could learn to recognize the physical patterns made by the Braille protrusions.

The second solution is for a visually-impaired person to have another person—someone who possesses adequate eyesight (a "sighted person")—accompany the said visually-impaired person in order to have the said "sighted person" read the cards on behalf of the said visually-impaired person for the purpose of transmitting to the said visually-impaired person the identity of the card(s) that is/are received by the said visually-impaired person. The problem with this method is that it is not always practical to find a third-person who is willing or able to attend a card game for an indefinite period of time where the sole function of said "sighted person" is to identify playing cards for a said visually-impaired individual. A further problem with this method is that it may be possible for the said visually-impaired person to receive advice (with respect to strategy) from the said "sighted person;" receiving any such advice would constitute cheating, and thus would be a prohibited activity if the said visually-impaired person were playing a game such as "poker" at a commercial establishment.

The third solution is to deploy a portable electronic device that has been designed at the University of Pittsburgh. A paper entitled *Playing Cards Reader for People with Visual Impairments*, Maria Toro, May 2010, describes a portable unit designed to read the identity of playing cards for a visually-impaired person. However, this method is inefficient because it requires a user to lift the card off of the table in order to insert the card into the device. The problem with this method is that it requires a visually-impaired player to accomplish the nearly-impossible task of lifting the cards off of the table without allowing any of the cards to be seen by any opponents who possess adequate eyesight to see the cards when they are lifted off of the table—this negates the possibility that privacy of information may be maintained.

2. Brief Description of Near Field Communications

Near Field Communications ("NFC") has a strictly-defined set of technical parameters that makes it different from other standards of communication. NFC operates across a practical physical distance of approximately zero (0) to ten (10) centimeters.

NFC allows a wireless connection to be established automatically between multiple devices where each device is NFC-enabled.

NFC utilizes electromagnetic induction in order to facilitate a transfer of information between at least two devices where each of the said devices is NFC-enabled; NFC may be configured to transfer information in one of two ways:

(i) an "active-active" manner, wherein at least two devices interact with each other, and wherein each device has disposed within it an active NFC apparatus (typically called an active "NFC Reader") that is coupled to a source of power where said source of power enables the said active "NFC Reader" to generate an electromagnetic field where said electromagnetic field enables each device to accomplish both the transmission of, and the reception of, information; or (ii) an "active-passive" manner, wherein at least two devices interact with each other, and wherein one of the devices utilizes a passive NFC apparatus (typically called a passive "NFC Tag"), while another device utilizes an active "NFC Reader." A passive "NFC Tag" is not coupled to any source of power, and is capable only of transmitting information that has been encoded within an NFC microchip that comprises part of the said passive "NFC Tag." A passive "NFC Tag" becomes activated when it comes physically within the electromagnetic field generated by an active "NFC Reader;" as a result of the said activation, said passive "NFC Tag" automatically transfers information that is encoded thereon to the said active "NFC Reader."

Regardless of which method is used to transfer information via the use of NFC, each device that is NFC-enabled must be equipped with at least the following three (3) basic components:

(i) at least one NFC microchip; and
(ii) at least one antenna; and
(iii) at least one rectifier.

Said antenna(e) and said rectifier(s) are microcircuits that are coupled to the said NFC microchip; the said antenna(e) and the said rectifier(s) must be coupled to the said NFC microchip in order to facilitate the transmission and/or the reception of information that is transferred via the deployment of NFC.

3. Description of the Prior Art Relating to the Present Invention

The prior art discloses inventions wherein microchips and microcircuits are embedded completely within playing cards in order to be read by external "reader" devices. However, each of the inventions comprising the prior art is substantively different from the present invention in two qualitatively significant ways: (i) each invention comprising the prior art deploys a technology whose practical purpose is different from NFC; and (ii) each invention comprising the prior art has an objective that is fundamentally different from that of the present invention. To underscore why these differences lend force to the argument that the present invention is indeed novel, it is worth noting that it would not be possible to create the present invention by deployment of the technologies that are shown in the prior art. This is true because deployment of the technologies shown by the prior art within the context of the present invention would allow for the interception by third parties of any transmission carrying the information regarding each individual playing card; this would defeat one of the purposes of the present invention—namely, ensuring the preservation of privacy of information with respect to the cards that are received by a player. The very short physical distance across which NFC transmits information makes NFC a highly secure way in which to accomplish the task of transferring information in situations where privacy of information is a priority. The necessity for the preservation of privacy of information when playing card games simultaneously makes: (i) the technologies shown in the prior art inherently ill-suited for application within the context of the present invention; and (ii) NFC inherently well-suited for application within the context of the present invention.

EP1713027 (invented by Koyama, et al.) discloses an integrated circuit embedded completely within a playing card. Koyama's invention further discloses a plurality of reader devices that are disposed within a table upon which a card game is being played. Koyama's invention is configured to provide a system that may be utilized by a commercial establishment in order to authenticate and to track the playing cards that are being used in any given game. The purpose of Koyama's invention is to facilitate the prevention of cheating by ensuring that only the said cards that are placed into play by the said commercial establishment are the ones that actually remain in play throughout the duration of any particular game.

DE102007007022 (invented by Ernst), and United States Patent Application 20070052167 (invented by Galatan), are explained together because they are designed for substantially similar purposes. The inventions by Ernst and Galatan each disclose a system wherein an apparatus deploying Radio Frequency Identification ("RFID") is embedded completely within a playing card, and each invention further discloses a plurality of reader devices that are disposed within a table upon which a card game is being played. The purpose of the inventions by Ernst and Galatan is to provide a mechanism by which a card game that is being played as part of a poker tournament is capable of being broadcast to an outside audience.

U.S. Pat. No. 7,727,060 (invented by Mills) discloses a system wherein an RFID apparatus is embedded completely within a playing card. The invention by Mills further discloses a reader device that is deployed by a commercial establishment in order to authenticate the said card as having been placed into play by the said commercial establishment. The purpose of the invention by Mills is to enable a commercial establishment to conduct card games wherein at least one of the participants is located physically at a live gaming table within the said establishment, and at least one of the participants is located physically in a location that is different from that of the said live gaming table.

United Stated Patent Application 20130178264 (invented by Vilpas) discloses a system wherein an RFID apparatus is embedded completely within a playing card. The invention by Vilpas further discloses a reader device that is deployed by a commercial establishment in order to track the said card during the progression of play. The purpose of the invention by Vilpas is to enable a commercial establishment to track the distribution of the individual cards that are placed into play during any given game in order to facilitate an improved presentation of the said card game to an outside audience.

BRIEF SUMMARY OF THE INVENTION

1. Components of the Present Invention

The object of the present invention is to deploy NFC technology as an aid to: (i) facilitate the ability of a person who is visually-impaired to ascertain the rank and the suit of an individual playing card; and (ii) ensure privacy of information regarding the identity of the said card for a user of the present invention. In accordance with the purposes of the present invention, as embodied and broadly described herein, the present invention includes:

A passive "NFC Tag" that is embedded completely within a playing card where the said passive "NFC Tag" is encoded with the information necessary to identify the specific rank and the suit of the said playing card; and A flexible tubular sheath that is configured to be deployed by being worn upon at least one finger of a human hand; and An active "NFC Reader" that is configured to: (i) generate an electromagnetic field in order to induce the said passive "NFC Tag" to transfer the information encoded thereon to the said active "NFC Reader;" and (ii) receive the said information from the said passive "NFC Tag;" and (iii) relay the said information to another member of the multi-part system described herein where said relay is accomplished via a physical wire or by wireless transmission; and A source of power that is disposed within the said flexible tubular sheath where the said source of power is coupled to the said active "NFC Reader;" and A physical or wireless conduit by which the said active "NFC Reader" may transmit electronically the said information received from the said passive "NFC Tag" to an earpiece that is configured to be worn by a user of the present invention; and At least one microchip disposed within the said earpiece where said microchip has encoded thereon: (i) a plurality of individual audio files (e.g., "mp3" files) where each said individual audio file corresponds to one of the unique combinations of rank and suit (e.g., "Eight of Clubs," "King of Hearts") that comprise a typical deck of playing cards; and (ii) software that is configured to process the said information that is received from the said active "NFC Reader" in a manner that causes the said microchip that is disposed within the said earpiece to execute the said individual audio file that corresponds to the unique combination of the rank and the suit of the individual playing card that is sought to be identified via the use of the present invention; and A source of power disposed within the said earpiece where said source of power is coupled to the said microchip that is disposed within the said earpiece; and A physical connection between the said microchip that is disposed within the said earpiece and a speaker that is disposed within the said earpiece where said speaker is configured to emit the said executed individual audio file in the form of an audible signal that may be heard easily, and that may be understood easily, by a said user of the present invention.

2. Advantages of the Present Invention

The present invention solves the underlying problems enumerated herein by providing an external aid that deploys NFC technology in order to facilitate the ability of a visually-impaired person to: (i) ascertain the unique identity of a playing card; and (ii) maintain privacy of information regarding the identity of the cards while the said visually-impaired person is utilizing the present invention.

The present invention eliminates the difficulty encountered by commercial establishments in trying to utilize Braille playing cards where such cards may: (i) be damaged by excessive use; or (ii) be damaged by mechanical card shufflers; or (iii) present the possibility that privacy of information regarding the identity of the cards becomes sacrificed as opponents possessing adequate eyesight learn to recognize the physical patterns made by the protrusions that are disposed upon the said Braille cards.

The present invention eliminates the necessity of a visually-impaired person to find a "sighted person" who is both willing and able to sit at a gaming table for an indefinite period of time.

The present invention eliminates the need for a visually-impaired person to master the nearly-impossible task of lifting the cards off of the table (in order to place them into a machine that will read them for the said visually-impaired person) without exposing any of the cards to any "sighted" opponents who are seated at the table.

The present invention avoids the possibility that a user would sacrifice privacy of information regarding the identity of the cards. This is true because NFC suffers from none of the inherent lack of security that is present in the technologies that have been deployed by the inventions comprising the prior art. As mentioned herein, if the technologies shown in the prior art were to be deployed within the context of the present invention, the present invention would be rendered impracticable because, unlike NFC, the technologies deployed by the inventions comprising the prior art are vulnerable to having their transmissions intercepted by third parties.

BRIEF DESCRIPTION OF THE SEVERAL VIEWS OF THE DRAWINGS

The accompanying drawings, which are incorporated in and form a part of the specification, illustrate exemplary embodiments of the present invention and, together with the description, serve to explain the principles of the present invention.

REFERENCE NUMERALS IN THE DRAWINGS

Figure 1:
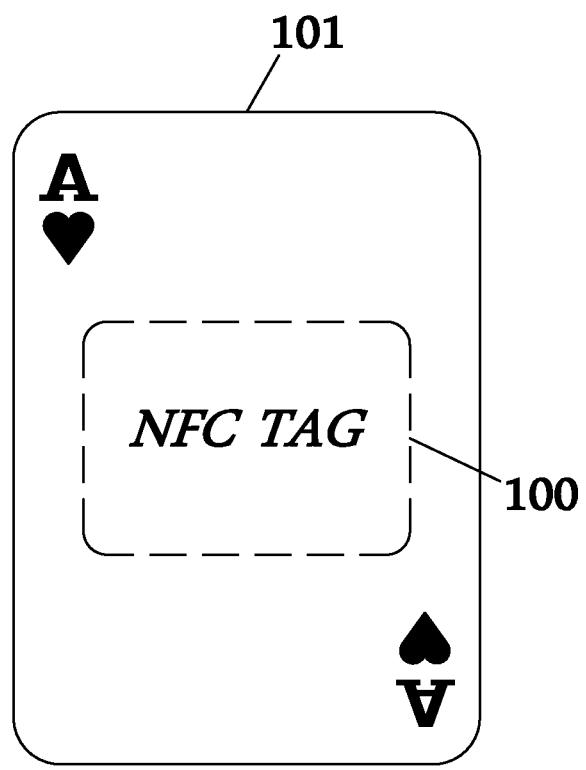
FIG. 1 shows a passive "NFC Tag" embedded completely within a playing card.

100 Passive "NFC Tag"
101 Playing card
102 Flexible tubular sheath
103 Active "NFC Reader"
104 Source of power coupled to active "NFC Reader"
105 Physical wire
106 Earpiece
107 Microchip disposed within earpiece
108 Source of power coupled to microchip disposed within earpiece
109 Speaker provided as one component of earpiece

DETAILED DESCRIPTION OF THE INVENTION

1. Detailed Explanation of the Present Invention

The present invention discloses a multi-part system that utilizes an "active-passive" configuration of NFC technology in order to: (i) facilitate the ability of a visually-impaired person to ascertain the specific rank and suit of a playing card; and (ii) maintain privacy of information regarding the unique identity of the said card for a said user of the present invention.

Referring to FIG. 1, a passive "NFC Tag" 100 is embedded completely within a playing card 101 where the said playing card is constructed of paper, plastic, or of any material that is suitable for the purpose of making a playing card. It is an object of the present invention that the said passive "NFC Tag" 100 be encoded with the information necessary to identify the specific rank and the suit of the said playing card 101 within which the said passive "NFC Tag" 100 is embedded. It is a further object of the present invention that the said passive "NFC Tag" 100 be configured to transmit the said information across a physical distance of not greater than ten (10) centimeters from the said passive "NFC Tag" 100.

Figure 2:
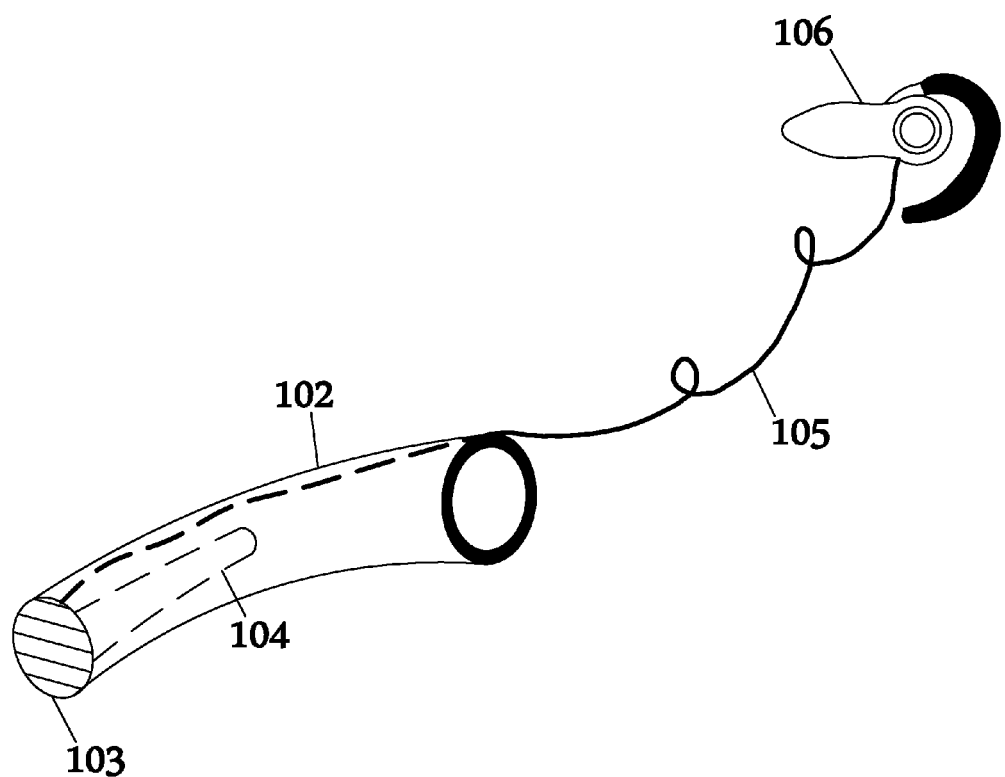
FIG. 2 shows a configuration of the present invention wherein a physical wire is utilized as the conduit by which information is transmitted from an active "NFC Reader" to an earpiece.

Referring to FIG. 2, a flexible tubular sheath 102 may be made of neoprene, silicone, or other suitable material. It is an object of the present invention that said sheath 102 be configured to be deployed by being worn upon at least one human finger of a human hand. However, it is understood that said sheath 102 may be configured in any manner that is appropriate for the purposes described herein.

Referring again to FIG. 2, an active "NFC Reader" 103 is disposed within said sheath 102, and is positioned approximately at or near one end of said sheath 102. It is an object of the present invention that the said active "NFC Reader" 103 be configured to generate an electromagnetic field in order to induce the said passive "NFC Tag" 100 to transfer the information encoded thereon to the said active "NFC Reader" 103. It is a further object of the present invention that the said active "NFC Reader" 103 be further configured to generate a said electromagnetic field that is not greater in size than that necessary to induce the said passive "NFC Tag" 100 to transmit the said information encoded thereon across a physical distance of not greater than ten (10) centimeters from the said passive "NFC Tag" 100. It is a further object of the present invention that the said transmission from the said passive "NFC Tag" 100 to the said active "NFC Reader" 103 be configured in a manner that protects the said transmission from being intercepted by an outside device. It is a further object of the present invention that the said active "NFC Reader" 103 be further configured to receive the said information from the said passive "NFC Tag" 100. It is a further object of the present invention that the said active "NFC Reader" 103 be further configured to relay the said information to an earpiece where said relay is accomplished via a physical wire or by wireless transmission 106 that is configured to be worn by a user of the present invention. It is a further object of the present invention that there be provided a conduit by which the said information is to be transmitted from the said active "NFC Reader" 103 to the said earpiece 106. It is a further object of the present invention that the said transmission from the said active "NFC Reader" 103 to the said earpiece 106 be configured in such a manner that protects the said transmission from being intercepted by an outside device. While one embodiment of the present invention shows a physical wire 105 being used as a conduit by which to transmit the said information from the said active "NFC Reader" 103 to the said earpiece 106, it is hereby understood by reference to FIG. 3 that the said transmission of the said information from the said active "NFC Reader" 103 to the said earpiece 106 may be accomplished by wireless means.

Referring again to FIG. 2, a source of power 104 for the said active "NFC Reader" 103 is disposed within the said sheath 102, and is coupled to the said active "NFC Reader" 103 in any manner that may be appropriate for the purposes described herein. In one embodiment of the present invention, said source of power 104 may be an ultra-thin flexible battery, but it is understood that said source of power 104 may be of any type that is appropriate for the purposes described herein.

Referring again to FIG. 2, one embodiment of the present invention is shown wherein a physical wire 105 is embedded at least partially within said sheath 102; said physical wire 105 may be of the type typically deployed by portable electronic devices for the purpose of transmitting information. In one embodiment of the present invention, the said physical wire 105 is attached at one end to the said active "NFC Reader" 103 and at another end to the said earpiece 106. It is an object of the embodiment shown in FIG. 2 that the said physical wire 105 should be utilized as a conduit by which to transmit the said information from the said active "NFC Reader" 103 to the said earpiece 106. While the embodiment shown in FIG. 2 contains a physical wire 105 that is used as the conduit for the said transmission of the said information, it is understood by reference to FIG. 3 that the present invention may be configured to not utilize a physical wire for the said purpose of transmitting the said information from the active "NFC Reader" 103 to the said earpiece 106, but to deploy instead a wireless method by which to accomplish the said transmission.

Figure 3:
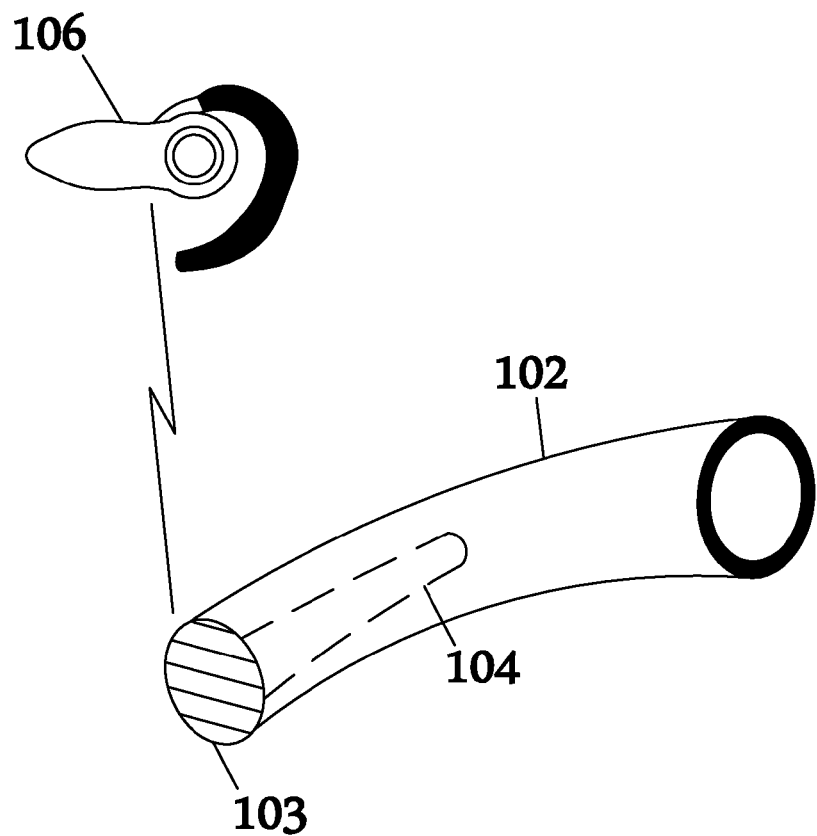
FIG. 3 shows an alternative configuration of the present invention wherein a wireless method is deployed to transmit information from an active "NFC Reader" to an earpiece.
Figure 4:
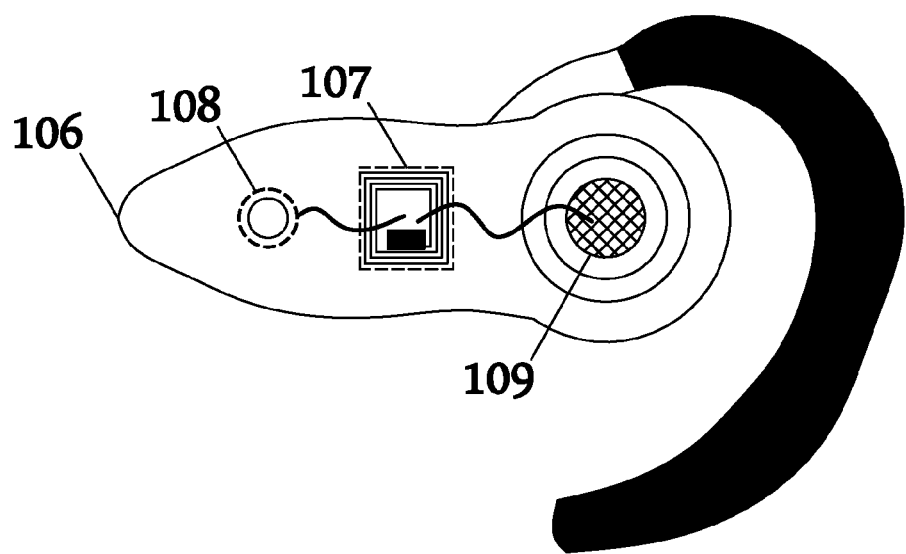
FIG. 4 shows an earpiece that is configured in accordance with the description of the present invention.

Referring again to FIG. 2 and to FIG. 3, a said earpiece 106 is constructed of hard plastic, soft plastic, or of any material that is appropriate for constructing an earpiece utilized typically in conjunction with a portable electronic device. It is an object of the present invention that there be disposed within the said earpiece 106 at least one microchip 107 upon which is encoded a plurality of individual audio files (e.g., "mp3" files) where each said individual audio file corresponds to one of the unique combinations of rank and suit (e.g., "Eight of Clubs," "King of Hearts") that comprise a typical deck of playing cards. It is a further object of the present invention that software be encoded upon the said microchip 107 where said software is configured to process the said information that is received from the said active "NFC Reader" 103 in a manner that causes the said microchip 107 to execute the said individual audio file that corresponds to the unique combination of the rank and suit of the individual playing card that is sought to be identified via the use of the present invention. It is a further object of the present invention to provide a source of power 108 that is disposed within the said earpiece 106 where said source of power 108 is coupled to the said microchip 107. It is a further object of the present invention to provide a physical connection between the said microchip 107 and a speaker 109 where the said speaker is disposed within the said earpiece 106, and where the said speaker 109 is configured to emit the said executed audio file as an audible signal, and to do so in a manner that may be heard easily, and that may be understood easily, by a said user of the present invention. It is a further object of the present invention that the said speaker 109 be configured to emit the said audible signal in a way that is capable of being heard only by a said user of the present invention.

2. Example of Implementation of the Present Invention

The present invention is intended to be appropriate for any type of game of cards where an individual player is required to: (i) ascertain the specific rank and the suit of at least one playing card during the course of a game; and (ii) do so while maintaining privacy of information regarding the identity of said card.

Each playing card is NFC-enabled by virtue of the fact that there is embedded completely within it a passive "NFC Tag;" each said passive "NFC Tag" is encoded with the information necessary to identify the specific rank and the suit of the said playing card within which the said passive "NFC Tag" is embedded.

When a user of the present invention receives at least one card during the course of a game, the said user deploys the device shown in either FIG. 2 or in FIG. 3 by placing the said device at a physical distance of approximately zero (0) to ten (10) centimeters from the said playing card.

An active "NFC Reader" that is disposed within the said device then induces the said passive "NFC Tag" to transfer the information that is encoded thereon to the said active "NFC Reader." The process of the said transfer of information takes place automatically, which means there is no requirement that a said user of the present invention undertake any action beyond merely placing the said active "NFC Reader" within a physical distance of zero (0) to ten (10) centimeters of a said playing card within which a said passive "NFC Tag" is embedded. Accordingly, it is not necessary for the purposes described herein for a said playing card to be lifted off of the table in any way.

Once the said active "NFC Reader" has received the information from the said passive "NFC Tag," the said active "NFC Reader" then transmits the said information to an earpiece that is configured to be worn by a said user of the present invention; said transmission of the said information may be accomplished either by a physical wire or by wireless means.

Once the said information is received by the said earpiece, it is converted by the said earpiece into an audible signal that then is emitted by the said earpiece in a form that may be heard easily, and that may be understood easily, by a said user of the present invention.

It is understood that the descriptions and drawings disclosed herein are presented for purposes of illustration, and are neither meant to be exhaustive nor to be construed as being limiting in any way with respect to the precise form of the present invention. It is further understood that further features of the present invention will become apparent to those who are skilled in the art to which the present invention relates. It is further understood that the present invention may be constructed of any type of materials that are suitable for the purposes described herein. It is further understood that the present invention may be manufactured in any manner that is appropriate for the purposes described herein.

Having described my invention, I claim:

1. A playing card system adapted to be used by the visually-impaired comprising:
   (a) a set of playing cards,
   (b) a set of passive NFC devices, one of said passive devices being attached to each of said cards,
   (c) each of said passive NFC devices containing coded card identification of the card to which the one of said passive devices is attached,
   (d) a housing adapted to be worn on a finger of a human hand,
   (e) a NFC reader attached to said housing,
   (f) said NFC reader adapted to read said coded identification of each of said cards when said reader is positioned in proximity to one of said passive NFC devices to provide an output coded signal,
   (g) an earpiece adapted to be worn by a human,
   (h) said earpiece containing decoding circuitry and a speaker,
   (i) means to couple said output coded signals of said NFC reader to said decoding circuitry,
   (j) said earpiece containing a set of audio files, each of said audio files corresponding to a separate one of said card identifications,
   (k) said earpiece being responsive to each of said output coded signals of said reader to execute the one of said audio files that corresponds to the one of said cards represented by the one of said output coded signals,
   (l) the execution of an audio file providing audio information through said speaker to the wearer of said earpiece.

2. The playing card system of claim 1 wherein: said NFC reader is limited to reading said passive NFC devices only across a physical distance that is less than a predetermined magnitude.

3. The playing card system of claim 2 wherein: a physical wire is said means to couple said reader output coded signal to said earpiece.

4. The playing card system of claim 2 wherein: wireless transmission is said means to couple said reader output coded signal to said microchip of said earpiece.

5. The playing card system of claim 1 wherein: a physical wire is said means to couple said reader output coded signal to said earpiece.

6. The playing card system of claim 1 wherein: wireless transmission is said means to couple said reader output coded signal to said microchip of said earpiece.

* * * * *